US006521432B1

(12) United States Patent
Powell et al.

(10) Patent No.: US 6,521,432 B1
(45) Date of Patent: Feb. 18, 2003

(54) METHODS FOR ENHANCING THE RATE OF MODIFICATION OF METASTABLE BONDS

(75) Inventors: Michael J. Powell, Gaithersburg, MD (US); Anthony R. Rees, Bethesda, MD (US); Paul M. Booth, Germantown, MD (US); Wonpyo Hong, Potomac, MD (US); Richard C. Titmas, Rockville, MD (US); Richard J. Massey, Rockville, MD (US)

(73) Assignee: IGEN International, Inc., Gaithersburg, MD (US)

( * ) Notice: Subject to any disclaimer, the term of this patent is extended or adjusted under 35 U.S.C. 154(b) by 0 days.

(21) Appl. No.: 08/479,849

(22) Filed: Jun. 7, 1995

Related U.S. Application Data

(63) Continuation of application No. 08/132,121, filed on Oct. 5, 1993, now abandoned, which is a continuation of application No. 07/837,660, filed on Feb. 14, 1992, which is a continuation of application No. 07/364,077, filed on Jun. 8, 1989, and a continuation-in-part of application No. PCT/US89/01951, filed on May 4, 1991, and a continuation-in-part of application No. PCT/US89/01950, filed on May 4, 1989, which is a continuation-in-part of application No. 07/190,271, filed on May 4, 1988.

(51) Int. Cl.$^7$ .............................. C12N 9/00; C07K 16/42
(52) U.S. Cl. ................................ 435/188.5; 530/388.9; 530/389.8
(58) Field of Search .............................. 435/188.5, 219, 435/232, 68.1; 530/388.9, 389.8, 404, 405, 406

(56) References Cited

U.S. PATENT DOCUMENTS 4,900,674 A * 2/1990 Benkovic et al. ............ 435/232
5,190,805 A * 3/1993 Schultz ........................ 435/108

FOREIGN PATENT DOCUMENTS

WO  WO-A-8 910 754  11/1989

OTHER PUBLICATIONS

Liottz, L. J., et al, (1993) J. Am. Chem. Soc. 115, 350–351.*
Gibbs, R.A., et al, (1992) Science 258, 803–805.*
Janda, K. P., et al, (1991) Tetrahedron 47, 2503–2506.*
Janda, K. D., et. al. (1988) Science, 241,1188–1191.*
Luta, R., et. al. (1988) Biochemistry 27, 7671–7677.*
Stephenson, R.C., et. al. (1989) J. Biol. Chem. 264, 6164–6170.*
Geiger, T., et. al, (1987) J. Biol. Chem. 262, 785–794.*
Kossiakoff, A.A. (1988) Science 240, 191–194.*
M. J. Darsley et al., *EMBO J.*, 1985, 4, 383–392.
U. K. Laemmli, *Nature* 1970, 227, 680–685.
R. J. T. Corbett and R. S. Roche. *Int. J. Rept. Prot. Rel.*, 1986, 28, 549–559.
A. Fontana, *Biophysical Chem.*, 1988, 29, 181–193.
A. Fontana et al., *Biochemistry*, 1986, 25, 1847–1851.
J. K. Blodgett et al., *J. Am. Chem. Soc.*, 1985, 107, 4305–4313.
C. van der Auwera et al., *Int. J. Rept. Prot. Res.*, 1988, 42, 186–191.
Anteuris et al., *Int. J. Rept. Prot. Res.*, 1988, 31, 391–310.
B. D. Walker et al., *P.N.A.S. USA*, 84, 8120.
M. M. Campbell et al., *JCS Chem. Comm.*, p. 730 (1980).
R. N. Scribner, *Tetrahedron Letters*, 43 (1976) 3853–3856.
M. Kolb et al., *Tetrahedron Letters*, 27, 4437–4440 (1986).
J. F. Normant et al., *Bull. Soc. Chim. Fr*, (1974) 2072.
S. Clarke, *Int. J. Pept. Protein Res.*, 1987, 30, 808–821.
A. Tramantano et al., *Science*, 1986, 234, 1566.
R. Sugasawara, M. Powell, et al. *J. Am. Chem. Soc.*, 1987, 109, 2174.
D. Y. Jackson et al., *J. Am. Chem. Soc.*, 1988, 110 4841.
D. Hilvert et al., *P.N.A.S. USA*, 1988, 85, 4953.
A. D. Napper, S. J. Benkovic, et al., *Science*, 1987, 237, 1041.
B. L. Iverson et al., *Science*, 1989, 243, 1184–1187.
Socher et al., *P.N.A.S. USA*, 1987 84, 8829–8833.
Laskey et al., *Cell*, 1987, 50, 975–985.
Y. Vo. Quang, *J. Med. Chem.* 29, 579–587 (1986).
Erhan and Greller, *Nature*, vol. 251, p. 353 (1974).
Stedman's Medical Dictionary, pp. 88, 89, 479 (24th Ed. 1982).
Iverson et al., *Science*, vol. 243, pp. 1184–1188 (Mar. 3, 1989).
Sudhir Paul et al., *Science*, vol. 244, pp. 1158–1162 (Jun. 9, 1989).

* cited by examiner

*Primary Examiner*—Charles L. Patterson, Jr.
(74) *Attorney, Agent, or Firm*—Barry Evans, Esq.; Kramer Levin Naftalis & Frankel LLP

(57) ABSTRACT

Antigens capable of eliciting antibodies which can enhance the rate of chemical reactions at peptide bonds are disclosed. In particular, the rate of cleavage or formation of metastable peptide bonds, such as ASN-X, ASP-X, GLN-X, GLU-X, LYS-X, and HIS-Y-X, where X and Y are any amino acid, is enhanced by antibodies elicited by said antigen.

12 Claims, No Drawings

METHODS FOR ENHANCING THE RATE OF MODIFICATION OF METASTABLE BONDS

This application is a continuation of application Ser. No. 08/132,121, filed Oct. 5, 1993 now abandoned, which is a continuation of Ser. No. 07/364,077, filed Jun. 8, 1989 which is a continuation of Ser. No. 07/837,660, filed Feb. 14, 1992, which is a continuation-in-part of Ser. No. 07/190,271, filed May 4, 1988, and a continuation-in-part of PCT/US89/01950, filed May 4, 1989 and a continuation-in-part of PCT/US89/01951, filed May 4, 1991.

FIELD OF THE INVENTION

This application is a continuation-in-part of commonly assigned applications U.S. Ser. No. 190,271, filed May 4, 1988, PCT/US89/01950, filed May 4, 1989, and PCT/US89/01951, filed May 4, 1989. The subject matter of said applications is incorporated by reference.

This invention relates generally to methods for enhancing the rate of cleavage or formation of peptide bonds. More particularly, this invention relates to methods for enhancing the rate of cleavage or formation of specific metastable peptide bonds within protein or peptide molecules by contacting such molecules with a rate-enhancing antibody.

Several publications are referenced in this application by Arabic numerals within parenthesis. Full citation for these references are found at the end of the specification immediately preceding the claims. The references more fully describe the state of the art to which this invention pertains as well as certain aspects of the invention itself.

BACKGROUND OF THE INVENTION

It is known that certain peptide sequences in proteins are metastable. These sequences, also referred to as "sensitopes," are susceptible to spontaneous chemical reactions such as deamidation, isomerization, racemization, and in some cases peptide bond cleavage. As such, they may be target sites for antibodies that enhance the rate of chemical reactions that occur at such sensitive sites.

It is known that certain synthetic peptide sequences are particularly susceptible to spontaneous reactions (1). Asparagine, aspartic acid, glutamine and glutamic acid are amino acid residues that are frequently associated with susceptible sequences, and it has been proposed that the amino acid residues flanking these particular side chains can determine the particular susceptibility of these sites within peptides (2). It has also been observed that the structural features around these sites in intact proteins can also influence the stability of these sites to spontaneous chemical modification (3).

More specifically, it is known that polypeptides containing the dipeptide sequences, ASN-PRO, ASN-GLY, ASP-PRO, ASP-GLY GLN-X or GLU-X, wherein X is any amino acid, undergo hydrolysis at a much higher rate than other dipeptides. This instability is due to the formation of a cyclic structure resulting from intramolecular attack of the side chain amide or acid on the peptide bond between the two amino acids. However, these metastable bonds are reported to be more stable in native (not denatured) proteins (2).

Antibodies have previously been generated that catalyze acyl transfer reactions (4), sigmatropic rearrangements (5), intramolecular cyclization (6), and peptide bond hydrolysis (7). It has been speculated that such antibodies may be particularly suited to performing substrate assisted catalysis—i.e., catalyzing the reaction of a substrate containing a reactive nucleophile or catalyst within the molecule undergoing transformation.

It is known that antibodies raised against peptides are able to bind to the same sequence when the latter are located within an intact protein. For example, antibodies elicited against a peptide comprising amino acids 1–15 of tumor necrosis factor (TNF) are able to bind to native tumor necrosis factor and in doing so, inhibit its interaction with a cell surface receptor (8). Similarly, antibodies against a peptide comprising amino acids of the gp 120 coat protein from HIV cross-react with the intact virus and inhibit the interaction of the virus with its cellular receptor, CD4 (9). In another example, monoclonal antibodies raised against a peptide comprising amino acids 67–83 of hen egg lysozyme were able to cross-react with the intact protein and are able to recognize other avian species of lysozyme whose sequences within the epitope are substantially similar (10).

While methods for preparing catalytic antibodies have been described, and while methods for binding noncatalytic and catalytic antibodies to antigens or substrates of interest have been described, the art has heretofore not provided methods of enhancing the rate of cleavage or formation of certain metastable peptide bonds known to undergo spontaneous hydrolysis.

OBJECTS OF THE INVENTION

It is a primary object of this invention to provide methods for enhancing the rate of cleavage or formation of metastable peptide bonds within protein or peptide molecules.

It is a further object of the invention to provide methods for enhancing the rate of cleavage or formation of metastable peptide bonds, e.g., ASN-PRO, ASN-GLY, ASP-PRO, ASP-GLY, GLN-X or GLU-X, wherein X is any amino acid, by contacting the peptide or protein molecule containing the metastable peptide bond with a rate-enhancing antibody which is prepared by a rational design method according to the invention.

It is still a further and related object of the invention to provide methods for enhancing the rate of hydrolysis of specific peptide bonds in protein or peptide molecules by contacting such molecules with a rate enhancing antibody which promotes the natural tendency of these bonds to form a cyclic intermediate structure by intramolecular attack of the amide or acid group of the aspartic or glutamic acid or asparagine or glutamine side chains on the peptide bond.

SUMMARY OF THE INVENTION

These and other objects of the invention are achieved in an antigen for elicitation of a rate-enhancing antibody, said antigen containing a hapten having a metastable bond.

One embodiment of the invention is an antigen for elicitation of an antibody capable of enhancing the rate of reaction of a substrate of interest at the site of a metastable bond, said antigen containing a hapten which mimics said substrate of interest at or near the said site of said metastable bond.

A further embodiment of the invention is an antibody which enhances the rate of modification of a metastable bond in a substrate of interest, said antibody having been prepared by a process comprising the steps of: selecting the specific metastable bond to be modified; selecting an antigen comprising a hapten which mimics said substrate at or near the said site of said metastable bond; exposing cells capable of producing antibodies to said antigen and thereby generating antibody producing cells; hybridizing said antibody producing cells with myeloma cells and thereby generating a plurality of hybridoma cells each producing monoclonal antibodies; and screening said plurality of monoclonal antibodies to identify a monoclonal antibody which binds to an epitope at or near the metastable bond to be modified and enhances the rate of modification of said metastable bond.

A further embodiment of the invention is a method for preparing antibodies which enhance the rate of cleavage or formation of a metastable bond of interest comprising the steps of: selecting the specific metastable bond to be cleaved or formed in a protein or peptide molecule substrate of interest; selecting an antigen comprising a hapten which mimics said substrate at or near the said site of said metastable bond; exposing cells capable of producing antibodies to said antigen and thereby generating antibody producing cells; hybridizing said antibody producing cells with myeloma cells and thereby generating a plurality of hybridoma cells each producing monoclonal antibodies; and screening said plurality of monoclonal antibodies to identify a monoclonal antibody which binds to an epitope at or near the metastable bond to be modified so as to enhance the rate of modification of said metastable bond.

A yet further embodiment of the invention is a method for enhancing the rate of modification of a specific metastable bond within a protein or peptide molecule substrate of interest which comprises contacting said substrate with an antibody under conditions sufficient for said antibody to bind to said substrate at an epitope at or near said specific metastable bond and to enhance the rate of reaction.

A still further embodiment of the invention is a method for enhancing the rate of modification of a specific metastable bond within a protein or peptide molecule substrate of interest which comprises contacting said substrate with an effective amount of an antibody, under conditions sufficient for said antibody to bind to said substrate at an epitope at or near said specific metastable bond, and thereby enhance the rate of said reaction, said antibody having been produced by the method of: selecting the specific metastable bond to be modified; selecting an antigen comprising a hapten which mimics said substrate at or near the said site of said metastable bond; exposing cells capable of producing antibodies to said antigen and thereby generating antibody producing cells; hybridizing said antibody producing cells with myeloma cells and thereby generating a plurality of hybridoma cells each producing monoclonal antibodies; and screening said plurality of monoclonal antibodies to identify a monoclonal antibody which binds to an epitope at or near the metastable bond to be modified.

The invention, as well as other objects, features and advantages thereof will be understood more clearly and fully from the following detailed description.

DETAILED DESCRIPTION OF THE INVENTION

The invention embodies an antigen wherein the metastable bond is selected from the group consisting of ASN-X, ASP-X, GLN-X, GLU-X, LYS-X, and HIS-Y-X, where X and Y are any amino acid.

In particular, the invention embodies an antigen containing a hapten which is immunologically cross reactive to an amino acid sequence at or near the said site of said metastable bond.

More in particular, the invention embodies an antigen wherein said hapten is comprised, of an amino acid sequence of at least two amino acids.

Still more in particular, the invention embodies an antibody elicited by said antigens wherein the said metastable bond is selected from the group consisting of ASN-X, ASP-X, GLN-X, GLU-X, LYS-X, AND HIS-Y-X, wherein X and Y are any amino acid and, wherein the identity of the said metastable bond is determined by subjecting the substrate of interest to modification under art-known conditions and analyzing the products obtained in such modification.

Definition of Terms

In its broadest sense, the term "antigen" is defined as a molecule which induces the formation of an antibody. As used herein, the term "antigen" means a molecule which is inherently immunogenic, a hapten according to the invention or an immunogen which comprises a hapten according to the invention coupled to a carrier molecule by a suitable coupling moiety. Carrier molecules include, for example, keyhole limpet hemocyanin (KLH), thyroglobulin, chicken immunoglobulin, ovalbumin, bovine serum albumin (BSA), T-helper peptides, etc. "Coupling moieties" as used herein refer to biotechnological cross-linking reagents well known in the art (e.g., commercially available from Pierce, Rockford, Ill.) and include, for example, Traut's reagent, dissuccinyl suberate, etc.

The term "antibody" includes whole immunoglobulins and fragments thereof which contain the binding site for the antigen.

The term "rate enhancing antibody" refers to antibodies according to the invention which recognize and bind to epitopes on proteins or peptide molecules containing a metastable peptide bond and thereby stoichiometrically or catalytically (as these terms are defined below) enhance the rate of the reaction.

The term "metastable peptide bond" includes all bonds which have a propensity for undergoing spontaneous reactions of formation or cleavage. The term "spontaneous reaction" refers to a reaction at a specific position within a peptide sequence which proceeds at a rate higher than usually observed for peptide bonds. In particular, ASN-PRO, ASN-GLY, ASP-PRO, ASP-GLY, GLN-X or GLU-X, wherein X is any amino acid, are known to undergo a spontaneous peptide bond hydrolysis mediated by formation of a cyclic intermediate.

The term "dipeptide analog" as used herein refers to a structure in which the normal amide bond (i.e., —CO—NH—) between the two amino acids has been replaced by an array of atoms as defined above. Additional amino acid residues may be incorporated to surround the dipeptide analog to form a polypeptide. The moieties surrounding the dipeptide analog contain peptide bond linkages which can be altered such that the naturally occurring C=O group is replaced by NH, O, S, $CH_2$, $CF_2$ or C=S and/or the naturally occurring NH group is replaced by O, S, $CH_2$, $CF_2$, C=O or C=S. For example, the moieties can be retropeptides in which the C=O and NH groups of the amide bonds are interchanged.

The term "hapten" as used herein is defined as a molecule which can act as an epitope. Haptens may contain an amino acid sequence of at least two amino acids which are identical to or mimic the region of a peptide or protein containing the metastable bond of interest. A hapten may also comprise an analog such as a dipeptide analog as heretofore defined.

The term "naturally occurring amino acid" as used herein includes the twenty essential alpha-amino acids and other alpha-amino acids which may or may not be found in proteins. These amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, 4-hydroxyproline, 5-hydroxylysine, epsilon-N-methyllysine, 3-methylhistidine, beta-alanine, gamma-aminobutyric acid, homocysteine, homoserine, citrulline, ornithine, canavanine, djenkolic acid and beta-cyanoalanine. An amino acid consists of a carbon atom to which is bonded an amino group, a carboxyl group, a hydrogen atom and a distinctive group referred to as a "side chain." The term "analog of said side chain" as used herein is defined as a side chain of a naturally occurring amino acid in which one or more moieties of the naturally occurring side chain is replaced by one or more different moieties which substantially corresponds to the naturally occurring moiety. Those side chains containing a hydroxy group can be glycosylated, phosphorylated, sulphonylated or protected by a hydroxy protecting group. The hydroxy group of any of the side chains may be protected by any number of suitable hydroxy protecting groups well known in the art. These include, for example, a tertiary butyl ether group.

Binding of an antibody "at or near the site of interest" refers to binding of an antibody directly to the metastable bond of interest, binding to peptide sequences adjacent to the metastable bond of interest, or to binding both directly on the metastable bond of interest and on the amino acid sequences on one side or both sides of the metastable bond of interest.

A "catalytic" antibody is an antibody which is capable of changing the rate of a chemical reaction, all other conditions (e.g., temperature, reactant/substrate concentration, etc.) being the same, and which is not consumed in the reaction, and which has the capability of converting multiple moles of reactant/substrate per mole of catalytic antibody. From a mechanistic viewpoint, it binds the reactant/substrate, effects the accelerated conversion of the reactant/substrate to the product and then releases the product, changing the rate of the chemical reaction without shifting the position of the equilibrium. The aforementioned definitions are characteristics of ideal catalysts. However, in practice, even the best of catalysts become poisoned or deactivated by contamination in the reaction system or as a result of chemical or physical destruction during the reaction process. For reasons well known in the art, the true operation of a catalyst may be obscured by components of the reaction system or by the condition of the reaction environment. Rate enhancing antibodies directed to metastable peptide bonds may be described as catalytic antibodies if the antibody is released from the epitope after the reaction is complete.

A "stoichiometric" antibody is an antibody which enhances the rate of the chemical reaction stoichiometrically, i.e., it enhances the rate of the reaction, but unlike a catalytic antibody, is stoichiometrically consumed during the reaction. Rate enhancing antibodies directed to metastable peptide bonds may be described as stoichiometric antibodies if the antibody remains bound to the epitope after the reaction is complete or is altered by the reaction, and thus cannot promote additional reactions.

Identification of Protein or Peptide Molecules and Metastable Bonds Therein as Targets for Rate-Enhancing Antibodies Metastable bonds are the preferred modification sites for the methods of the invention. For example, sequences containing the following amino acid combinations, ASN-GLY, ASN-PRO, ASP-GLY, ASP-PRO, GLN-X, or GLU-X, wherein X is any amino acid, are known to be metastable in denatured proteins or small peptides and to undergo spontaneous hydrolysis. When present in a native protein, these bonds are more stable, but the binding of an antibody to an epitope at or in proximity to the metastable bond destabilizes the bond and enhanced rate of cleavage is obtained.

The identity and location of a metastable bond within a protein or peptide molecule of interest may be known or may be established by reference to various methods available to the art (11,12). Such information may be available in various forms and with various levels of precision and may include the three-dimensional structure of the protein or peptide molecule, computer models or predicted structures thereof, or hydrophilicity profiles.

An empirical method for identifying suitable metastable bonds includes subjecting the protein or peptide molecule of interest to art-recognized modification conditions for a time sufficient to permit modification to occur. One skilled in the art will appreciate that other methods can be used to induce autolysis, such as, for example, incubation of the protein in EDTA (ethylene diamine tetracetic acid) at varying temperatures (14–16), hydroxylamine (17) or dilute acids (18, 19), as well as varying the temperature.

Thereafter, the modified fractions can be identified and the metastable bonds at which modification has occurred can be identified.

Protein or peptide molecules which may advantageously be modified according to the methods of the invention include immunoglobulin E (hydrolysis), tumor necrosis factor (hydrolysis), and human immune deficiency virus (hydrolysis).

PREPARATION OF RATE-ENHANCING ANTIBODIES

Once the metastable bond to be modified has been identified by the method described above, an antigen can be obtained or synthesized for use in an immunological method for eliciting antibodies. The antigens are desirably small peptides or analogs thereof which contain the metastable bond of interest or an analog of that metastable bond of interest. The antigen then can be employed as an immunogen to elicit through either in vitro or in vivo techniques antibodies having the desired rate-enhancing properties.

Broadly, the method comprises exposing cells capable of producing antibodies to the immunogen and thereby generating antibody producing cells; hybridizing the antibody producing cells with myeloma cells and thereby producing a plurality of hybridoma cells each producing monoclonal antibodies; and screening the plurality of monoclonal antibodies to identify a monoclonal antibody which catalyzes the chemical reaction of interest. The monoclonal antibody so identified may then be replicated, again by either in vivo or in vitro techniques, to obtain a quantity sufficient to catalyze the chemical reaction of interest.

The preferred immunogens of the invention comprise peptides having metastable sites or amino acid side chains that can participate in the catalytic process by a substrate assisting mechanism. These include sequences comprising: ASN-X; ASP-X; GLN-X; GLU-X; LYS-X; and HIS-Y-X wherein Y and X are any amino acids. Other immunogens as may be found by these empirical hydrolysis-fragment analysis techniques of the invention may also be used. Immunogens comprising cyclic analogs designed to induce the peptide or protein substrate to undergo intramolecular catalysis by creating an antibody combining pocket complementary to a reaction pathway of the specific reaction to be catalyzed may also be used.

The detection of antibodies with the desired activity and specificity is achieved by screening the hybridomas once they have been elicited. For example, screening may be achieved by high performance liquid chromatography (HPLC) or spectrophotometric methods (ELISA). Monoclonal antibodies are elicited in vivo by modification of the technique disclosed by Koprowski et al. in U.S. Pat. No. 4,196,265, issued Apr. 1, 1980, which is hereby incorporated by reference. The details of that process are known in the art. A series of monoclonal antibodies directed to a specific antigen are prepared under suitable conditions. This involves first immunizing BALB/C mice with an appropriate antigen. The antigen comprises a hapten according to the invention bound to a peptide or other carrier molecule.

Antibody-producing lymphocytes are then removed from the spleens of the immunized mice and hybridized with myeloma cells such as SP2/0 cells to produce hybridoma cells. These hybridoma cells are then plated in the wells of microtiter plates. The series of monoclonal antibodies being produced by the hybridoma cells is screened under appropriate conditions to identify monoclonal antibodies which catalyze the desired reaction under appropriate conditions. Alternatively, the medium may be tested for antibodies that bind to the immunogen and the hybridomas producing these antibodies then expanded in tissue culture or grown in vivo. Screening may be conveniently accomplished by treating a standardized solution of the reactant with an aliquot of medium withdrawn from a microtiter well and measuring the presence of the desired product by conventional instrumental methods. This measurement may be readily conducted, for example by spectrophotometric methods or by gas-liquid or high pressure liquid chromatography. By comparison with standardized samples of the desired product or reactant, rates of reaction may be quantified. In this manner, wells containing hybridoma cells producing monoclonal antibodies are identified. The selected hybridoma cells are then cultured to yield colonies.

These colonies may be further propagated in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

Antibodies elicited with the immunogens of the invention are "site specific" in that they are designed only to catalyze modification of the metastable bond of interest. Likewise, these antibodies are designed only to catalyze the formation of bonds from the termini of moieties having certain structural conformations at those termini. Rationally designed immunogens according to the invention may be used to elicit a site specific antibody capable of cleaving bonds at specific sites in a protein or peptide molecule to produce two or more cleavage products or to catalyze the formation of bonds wherein those cleavage products having the right structural conformation are joined.

The invention is further described in the following examples.

EXAMPLES

Example I

Method for Determining Metastable Peptide Bonds in a Protein Using Human Immunodeficiency Virus Type 1 (HIV-1) Glycoprotein 120 (GP 120)

GP 120 is purified to homogeneity by methods well known in the art. The purified GP 120 is dissolved in 50 mM Tris.HCl buffer containing 10 mM $CaCl_2$, pH 9.0, to give a final concentration of 1 mg/ml and then heated at 55° C. for 48 hr. The reaction mixture is analyzed by SDS-polyacrylamide gel electrophoresis (Laemmli, 1970) to determine the fragmentation pattern. The gels are stained with Coomassie Brilliant Blue R-250 in order to visualize the protein bands. Bands migrating faster than the gp 120 band based on a comparison to molecular weight standards indicate cleavage of metastable bonds. The individual fragments produced by thermal autolysis are purified to homogeneity by HPLC and their identity is established by amino acid analysis after acid hydrolysis and sequencing. Comparison of all these data with the known amino acid sequence of gp 120 allows unambiguous identification of the fragments and thereby the metastable cleavage sites.

This method can readily be used for other peptides, proteins, glycoproteins, and peptidoglycans. One skilled in the art will appreciate that other methods can be used to induce autolysis, such as incubation of the protein in EDTA (ethylene diamine tetracetic acid) at varying temperatures, (14–16) hydroxylamine (17) or dilute acids (18, 19), as well as varying the temperature.

Example II

Synthesis of Analogs for Metastable Peptide Bond Cleavage

In a further aspect of the invention, antibodies elicited by immunogens comprising conformationally constrained peptide analogs accelerate the hydrolysis of normal peptides. Such immunogens are prepared from, for example, certain cyclic or acyclic peptide analogs.

This aspect of the invention utilizes analogs of the cyclic structures which are intermediates in the spontaneous reactions which these metastable bonds undergo at a much higher rate than do other peptide bonds. These intermediates result from intramolecular attack of the side chain amide or acid on the metastable peptide bond between two amino acids such as ASN-PRO, ASN-GLY, ASP-PRO, ASP-GLY, GLN-X or GLU-X where X is any amino acid. The analogs mimic the conformation of the metastable peptide bond during spontaneous hydrolysis.

Antibodies induced by such analogs prepared as immunogens bind to and promote the cleavage of particular metastable peptide bonds by inducing a change in the conformation of the metastable peptide bond of interest. By way of illustration, the syntheses of preferred peptide analogs are described below.

A. Synthesis of Cyclic Difluoroketone Haptens

Cyclic difluoroketone haptens are designed as conformational analogs of the chemical structures which mediate the spontaneous cleavage which the metastable peptide bonds ASN-GLY and ASP-GLY undergo at a much higher rate than do other dipeptide bonds.

Immunogens incorporating said haptens are designed to elicit the formation of antibodies that can induce cleavage at ASN-GLY and ASP-GLY bonds either alone or as part of an intact sequence. Incorporation of these isosteres into peptides proceeds by known peptide synthesis.

These haptens are synthesized according to Scheme 1:
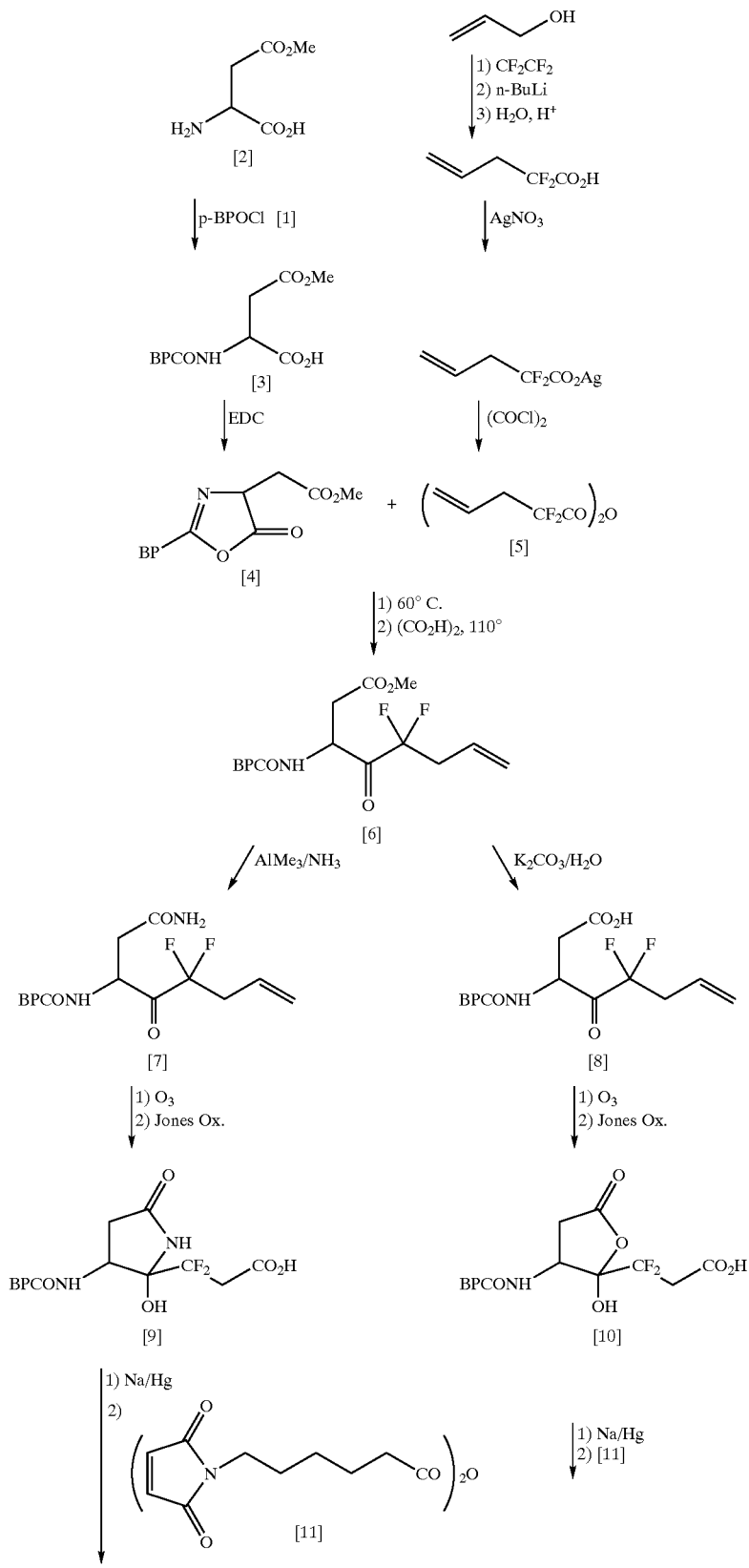
Scheme 1

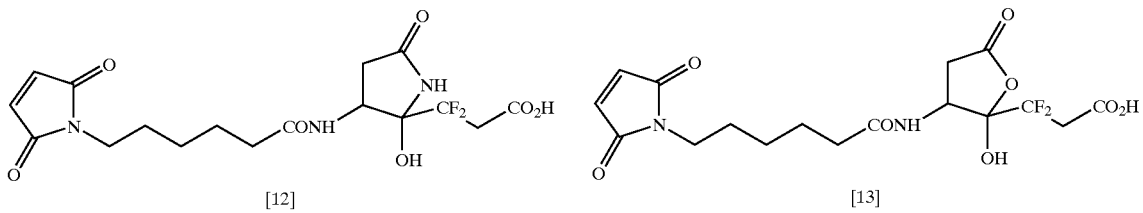

The synthetic methodology is essentially as described in Example 7 of Application Ser. No. PCT/US 89/01951 (filed May 4, 1989) with further modification to create the cyclic analog.

The compound 4-phenyl benzoyl chloride [1] is condensed with the monomethyl ester of aspartic acid [2] to yield the 4-phenylbenzoyl-protected analog [3]. Cyclization to the lactone [4] is achieved under aprotic conditions with 1-(3-dimethylaminopropyl)-3-ethyl-carbodiimide (EDC). Condensation with the anhydride J. F. Normant et al., *Bull. Soc. Chim. Fi.*, (1974) 2072 (25b) of the unsaturated difluoroketoacid [5] affords the dipeptide synthon [6] (25). Treatment of [6] with trimethylaluminium in liquid ammonia affords the protected asparagine synthon [7]. Ozonolysis to the aldehyde and Jones oxidation to the acid analog [9] proceeds smoothly. Deprotection of the 4-phenylbenzoyl group employing sodium amalgam (24) provides the ASN-GLY cyclic difluoroketone dipeptide synthon which can either be derivatised with the linker moiety [11] to provide [12] or alternatively incorporated into the required peptide sequence by methods known to the skilled artisan (26). Treatment of the protected dipeptide synthon [6] with potassium carbonate provides the aspartic acid-GLY synthon [8]. Similar.ozonolysis followed by Jones oxidation provides the ASP-GLY cyclic difluoroketone dipeptide synthon [10] which can either be incorporated into a selected sequence by methodology known to the skilled artisan (26), or directly derivatized with linker moiety [11] (24) for attachment to carrier protein.

B. Synthesis of Cyclic Phosphorus Containing Haptens

The phosphorus containing haptens produced by Scheme 2 (shown below), or immunogens incorporating said haptens, are designed to elicit antibodies that can induce cleavage at ASN-Y and ASP-Y, where Y is GLY or PRO, either alone or as part of an intact sequence. Incorporation of these phosphorus containing isosteres into peptides proceeds by known peptide synthesis.

This aspect of the invention utilizes phosphorus containing analogs of the chemical structures which mediate the spontaneous hydrolysis which the metastable peptide bonds ASN-Y, and ASP-Y, where Y is GLY or PRO, undergo at a much higher rate than do other dipeptide bonds.

By way of illustration, the syntheses of preferred phosphorus containing peptide analogs are described in Scheme 2.

The synthetic procedure for the cyclic phosphorus containing haptens essentially follows literature methodologies; however the analogs produced are novel compounds. Incorporation of the cyclic phosphorus isosteres into peptides proceeds by known peptide synthesis.

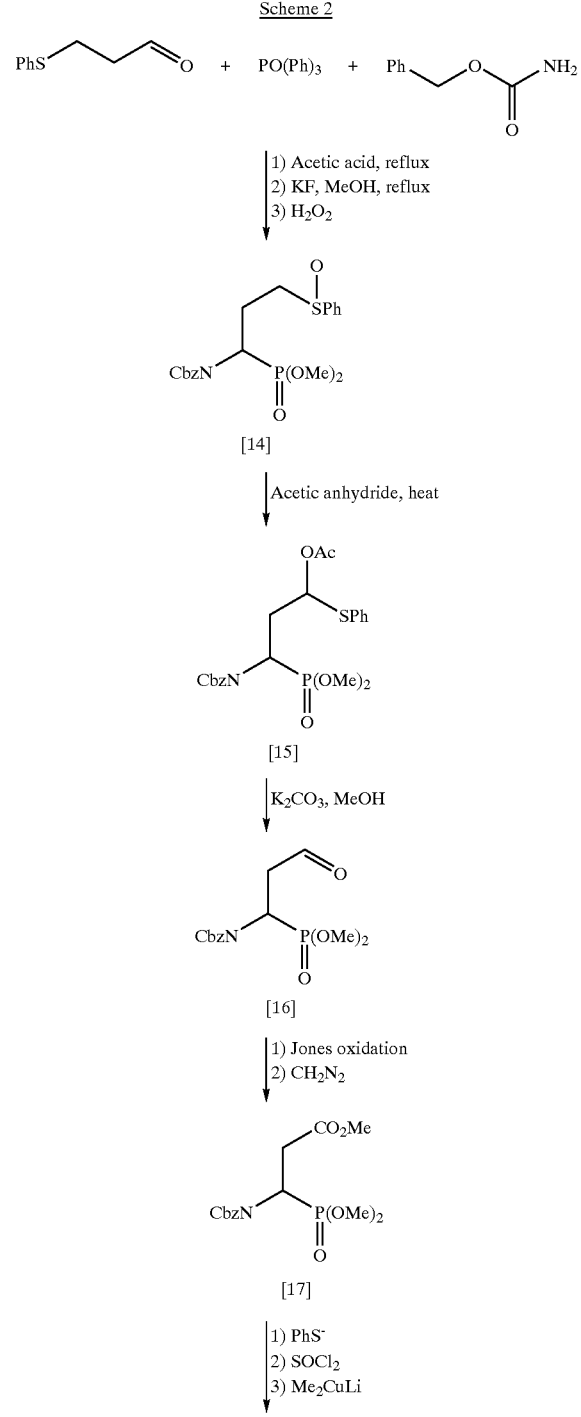

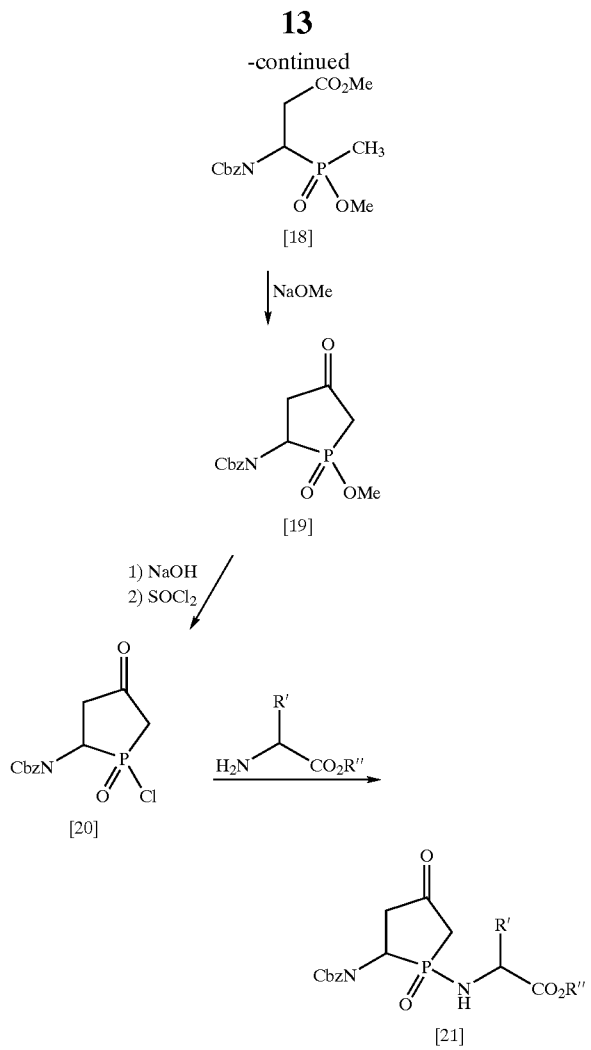

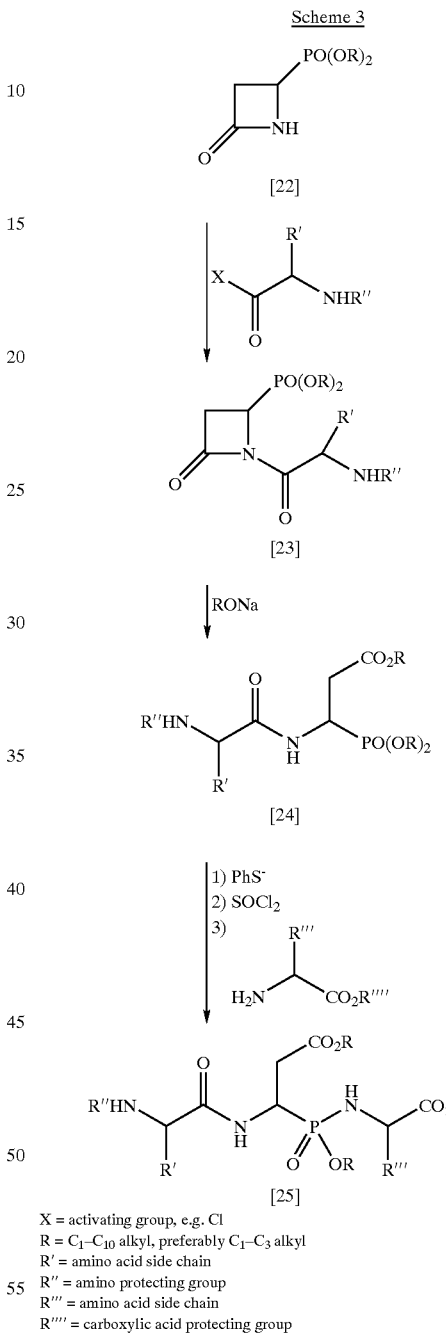

hydrolysis of particular metastable peptide bonds by inducing a change in the conformation of the metastable peptide bond of interest. By way of illustration, the syntheses of preferred phosphorus containing peptide analogs are described in Scheme 3.

The known sulfoxide (22) [14] is subjected to Pummerer rearrangement by heating in the presence of acetic anhydride to afford the α-acetoxy sulfide [15]. Mild base treatment selectively cleaves the acetoxy function, with concomitant expulsion of phenylsulfinyl anion to give aldehyde [16]; Jones oxidation followed by esterification with diazomethane leads to ester [17]. Selective mono-deprotection of a single methoxyphosphinyl group followed by treatment with thionyl chloride gives the phosphinoyl chloride which upon reaction with dimethyl copper lithium yields phosphonate [18]. Intramolecular Claisen-type cyclisation is achieved by exposure to sodium methoxide in methanol to give [19]. Base hydrolysis followed by treatment with thionyl chloride affords phosphonyl chloride [20] which is coupled with a suitably protected amino acid derivative to give the desired dipeptide analog [21].

C. Acyclic Phosphorus Tripeptide Analog for Metastable Bond Cleavage

Acyclic phosphorus containing haptens according to Scheme 3 (23) provide a broader cross reactivity than the haptens of A and B above. This aspect of the invention utilizes acyclic phosphorus containing analogs to the chemical structures which are intermediates of the spontaneous hydrolysis which the metastable peptide bonds, ASN-PRO, ASN-GLY, ASP-PRO, ASP-GLY GLN-X or GLU-X, wherein X is any amino acid, undergo at a much higher rate than do other dipeptide bonds.

Antibodies induced by such phosphorus containing analogs prepared as immunogens bind to and promote the X = activating group, e.g. Cl
R = $C_1$–$C_{10}$ alkyl, preferably $C_1$–$C_3$ alkyl
R' = amino acid side chain
R'' = amino protecting group
R''' = amino acid side chain
R'''' = carboxylic acid protecting group The known β-lactam derivative [22] (R=Me) is coupled with a protected amino-acid derivative in an analogous manner to that described in the literature, giving [23] (23). Alcoholysis of the β-lactam ring then gives the protected dipeptide derivative [24]. Selective cleavage of the phosphorus ester is achieved by treatment with thiophenolate anion. Chlorination of the resultant acid by reaction with thionyl chloride followed by coupling with a suitably protected amino acid affords the tripeptide analog [25].

Example III

In Vivo Elicitation of Catalytic Antibodies to a HIV gp 120 Coat Protein Using an Immunogenic Peptide A. Preparation of the Immunogen Once the metastable peptide bond of interest is selected as described in Example I, it is necessary to determine the optimal hapten for inducing rate enhancing antibodies. The optimal rate enhancing antibodies are induced by a hapten which is immunologically cross reactive with an epitope located at or near the metastable bond of interest. The hapten which will induce an antibody that will provide maximum rate enhancement must be determined empirically. Antibodies directed to different sites at or near the metastable peptide bond of interest are screened to determine which are rate enhancing, and of the latter, which are maximally rate enhancing.

A series of octapeptide sequences containing, or adjacent to, a metastable peptide bond identified by the methods described in Example I is synthesized. The sequences may either be homologous or identical to the amino acid sequence found in HIV gp 120, or contain a dipeptide or tripeptide peptide analog according to Example II, of the metastable peptide bond of interest. Such an analog replaces the naturally occurring amino acids defining the metastable peptide bond of interest at site or sites identified by the methods of Example 1, flanked on either side by up to seven amino acids. Thus, a nested set of octapeptides is generated containing either the metastable bond of interest, or a synthetic peptide analog of that metastable peptide bond of interest. This nested set of octapeptides is generated containing the metastable bond located between the same two amino acids but occurring at different distances from the N-termini of the peptides in each of the different octapeptides. Thus, the series of octapeptides may be visualized as having the metastable peptide bond of interest, or an analog, located at different positions. The corresponding antibodies induced by this series of octapeptides represents a panel of antibodies which bind at different distances from the metastable peptide bond of interest located in the native gp120 protein.

To better understand the nature of the haptens containing the metastable peptide bond (or analog thereto) of interest, consider the following twelve amino acid sequence containing a metastable bond within a target protein, presented only as an illustration:

V D R A S N P K A S T R

The following octapeptides might be constructed to be used as immunogens:

$NH_2$-V D R A S N-X-P K-COOH $NH_2$-D R A S N-X-P K A-COOH $NH_2$-R A S N-X-P K A S-COOH $NH_2$-A S N-X-P K A S T-COOH $NH_2$-S N-X-P X A S T R-COOH where N X P is the dipeptide isostere or the naturally occuring amino acid metastable dipeptide. It can thus be appreciated that it is possible to prepare a battery of haptens to induce a corresponding battery of antibodies which bind at a series of epitopes along the native protein sequence. This battery of antibodies is then screened to determined which are the preferred rate-enhancing antibodies.

Each peptide hapten is coupled to keyhole limpet hemocyanin (KLH) through a terminal cysteine residue utilizing the cross linker m-maleimidobenzoyl-N-hydroxy succinimide ester.

B. Preparation of Monoclonal Antibodies

BALB/C mice are immunized with the KLH-peptide conjugates (the immunogens) emulsified in complete Freund's adjuvant. A blood sample is obtained from each mouse and the serum separated by centrifugation and stored at 4° C. Sera obtained in this way are screened for binding activity to the original peptide immunogen by standard ELISA procedures. Antibody-producing mice immunized as described above and assayed for reactivity with the immunogens are sacrificed and their spleens removed and hybridoma cells are prepared using SP2/0 myeloma cells as the fusion partner.

C. Screening Hybridoma Cells Producing Catalytic Monoclonal Antibodies

Wells of plastic microtiter plates (Falcon 3915 Probind, Becton Dickinson Labware CAS, USA) are coated with 50 $\mu$L of peptide 5 $\mu$g/ml) in Tris.HCl buffer (0.1 M, pH 9.6).

Plates are first incubated for 30 minutes at 37° C. and then overnight at room temperature. After washing three times with Tween-containing phosphate-buffered saline (PBS-Tween 0.1% pH 7.4), 50 $\mu$l of serial dilutions of monoclonal antibodies in PBS-BSA 1% pH 7.4 are added in peptide-coated duplicate wells and incubated for 2 hrs. at 37° C. Plates are washed three times again with PBS-Tween 0.1% and wells are then treated with 50 $\mu$l of alkaline phosphatase-labeled goat anti-mouse IgG diluted 1:500 (Sigma, Mo., USA). Incubation is carried out for 1 hour at 37° C.

Additional extensive washing with PBS-Tween 0.1% is followed by incubation with 150 $\mu$L of alkaline phosphatase substrate (2 tablets/10 ml of Sigma 104–105) dissolved in 0.1 M glycine-NaOH buffer (pH 10.4) containing $MgCl_2$ and $ZnCl_2$, 1 mM. The enzymatic reaction is allowed to proceed for 2 hrs. at 37° C. and stopped by addition of 50 $\mu$L of $Na_2CO_3$ (1.5 M).

Absorbance is read at 405 nm in a Titertek Multiskan ELISA Reader (Flow Laboratories). Titer expression is determined by multiplying the optical density by the maximal dilution giving an absorbance three times as high as the negative control (consisting of pooled normal mouse sera diluted at 1:100).

Hybridomas giving a positive reaction in this screening assay are chosen for further study. IgG is purified from ascites fluid by HPLC with a Bakerbond $AB_x$ HPLC column.

D. Catalysis of Peptide Cleavage by Catalytic Antibodies Specific of HIV gp 120 Coat Protein The octapeptide substrates (2.7 $\mu$M containing, or adjacent to, the metastable bond (2.7 $\mu$M) are incubated with the catalytic antibodies produced by the procedure outlined above and the reaction monitored by reverse phase HPLC analysis of the mixture. The reaction is carried out at various pH values to determine the optimum pH for high $k_{cat}$ by the catalytic antibody. The reaction is followed using tritium-labelled octapeptide substrates prepared by acetylation of either the free octapeptide or the linker-peptide conjugate described above with $^3$H acetic anhydride (4–10 ci/mmol; Amersham). HPLC is then used to follow the production of tritium labelled cleavage product.

Antibodies that show the best $k_{cat}$ values for cleavage of the octapeptide substrate are tested for their ability to inhibit virus replication.

The virus replication assay is carried out essentially as described in the literature (20) except that cultures are propagated in microtube wells containing 200 $\mu$L. Graded concentrations of purified monoclonal antibodies, each in 25 $\mu$L, are preincubated for 1 hr. at 37° C. in 5% $CO_2$ with 50 $TCID^{50}$ HTLV IIIB in 25 $\mu$L. Following preincubation, H9 cells ($1\times10^5$ cells in 150 $\mu$LRPM1-040 supplemented with 20% heat inactivated FCS) are added to the wells, yielding final antibody concentrations ranging from 0.1 μg/ml to 10 μg/ml. Microtiter plates are incubated at 37° C. in 5% $CO_2$ for 14 days. Cells are fed by exchanging 100 μL cell-free supernatant fluid on days 3, 7, and 10 with fresh medium, and no further antibody is added during this period. Cell-free supernatant fluid (100 μL is analyzed for p24 antigen by RIA (DuPont, NEK-040). Since the amount of p24 correlates with the degree of infection and replication of the virus, those wells treated with catalytic antibodies having significant decreases in p24 when compared to virus treated with control antibodies demonstrate the inhibition resulting from cleavage of gp 120 by the catalytic antibody.

The C8166 fusion assay is described in the literature (21). Monoclonal antibodies are tested in 2 hour assays. H9 cells ($1\times10^4$) infected chronically with HTLV-IIIB are preincubated with varying concentrations of antibody in 150 μL medium in 96-well plates. All assays are done in triplicate. After 1 hour incubation at 37° C. in 5% $CO_2$, $3\times10^4$ C8166 cells (HTLV-I transformed umbilical cord lymphocytes) in 50 μl are added to the wells. Final well concentrations of antibodies are 31 μg/ml and 5 μg/ml. Preincubation with OCT4A (Ortho Diagnostics) at 25 μg/ml served as a control. After the plates are incubated for 2 hours at 37° C. in 5% $CO_2$, syncytia (ballooning cytoplasm greater than three lymphocyte cell diameters) are counted. To prevent bias during counting, samples are coded.

The antiviral activity of each monoclonal antibody is examined in HIV-I replication and cell fusion assays. Results show the dose dependent inhibition of virus infection by monoclonal antibodies.

The catalytic monoclonal antibodies elicited by immunization with peptides containing metastable bonds can prevent infection by HIV virus by causing rupture of an important region of the viral coat protein involved in binding to the CD4 receptor on lymphocytes. The catalytic monoclonal antibodies break the peptide bond in the chosen sequence in a manner analogous to the action of proteolytic enzymes. The mechanism of the antibody catalyzed hydrolysis of the octapeptide or gp 120 may or may not involve a metal ion but in either case may involve either a nucleophile in the active site of the antibody or nucleophilic addition of water activated by the antibody combining site.

Example IV

Methodology for the Production, Screening, and Isolation of Monoclonal Antibodies that Cleave Human IgE and Prevent Allergic Reactions Background The role of IgE in initiation of allergic responses has been the subject of extensive study for over 60 years. These studies have led to detailed understanding of the pathway for the allergic reaction. The primary event in the initiation of the allergic reaction is the binding of the allergen (antigen) to IgE. This results in crosslinking of the IgE on the surface of mast cells and basophil cells, the IgE being bound via its Fc region to Fc receptors present on the target cells. The consequence of this crosslinking is to trigger the release of histamine, SRS-A and other vasoactive amines which ultimately lead to the deleterious effects of an allergic response via their effect on other tissues in the body.

The IgE molecule has been functionally divided into two parts defined by their binding activities. This is demonstrated when the molecule is subjected to papain proteolysis which generates two fragments. The consequences of this proteolysis is to inactivate the IgE with respect to its ability to elicit allergic reactions. In fact, it becomes an inhibitor via blockade of Fc receptors with Fc fragments.

In order to generate an antiallergic monoclonal antibody, catalytic antibodies are prepared which are able to specifically cleave IgE and inactivate it without other deleterious effects. To achieve this, monoclonal antibodies are elicited with a cyclic dipeptide analog contained within the sequence of interest. Catalytic monoclonal antibodies so elicited will cause cleavage of the native IgE peptide sequence at the position shown:

CADSN | PRGVSAYLSRPSPFDLFIRKSPTITC cleavage site

This sequence is located between the CH2 and CH3 domains of IgE, cleavage of which will disrupt the activity of the IgE molecule and inhibit generation of an allergic response.

In order to raise a catalytic antibody to this region, the peptide hapten ADS(X)RGV, where (X) represents the cyclic dipeptide analog shown above, is synthesized by standard solid or solution phase methods. The completed peptide is fully deprotected and, if solid phase synthesis is used, cleaved from the solid support using trifluoroacetic acid. The N-terminal amino group of the peptide allows it to be attached to a carrier protein for immunization of mice.

A. Preparation of the Immunogen

1. Peptide Synthesis

The peptide hapten is synthesized by the solid phase technique using the polyamide-Kieselguhr composite resin. The side chain protection groups are the following: O-tert-butyl (tyrosine, aspartic acid, glutamic acid, serine, threonine); N-4-methoxy-2,3,6,-trimethyl benzenesulphonyl, (arginine). The temporary protection of the N-function is by fluorenylmethoxycarbonyl which is removed in 10 minutes with piperidine/DMF: 20/80. The coupling reactions are carried out using FMOC-amino acid anhydrides. The protected peptidyl-resin is fully deprotected by treatment with trifluoroacetic acid/thioanisole/m-cresol/thiophenol/ethanedithiol solution: 90/2/2/2/4 for three hrs. After filtration, the filtrate is concentrated under vacuum to a small volume. Ether is added to give a precipitate of the peptide. The ethereal supernatant is removed and the peptidic precipitate is washed twice with ether to yield the peptide hapten Ala-Asp-Ser-(X)-Arg-Gly-Val wherein the bracketed moiety is the cyclic dipeptide analog shown below. The synthesis of X is essentially as described in Example II.

2. Conjugation of the Hapten to the Carrier Molecule

The peptide hapten as above is conjugated to keyhole limpet hemocyanin (KLH) using glutaraldehyde. Coupling efficiency is 50–80% as estimated by binding of a trace amount of Iodine-125 labeled peptide added to the reaction mixture.

Immunization and screening for catalytic antibodies is performed essentially as described above.

C. Catalysis of Peptide Cleavage by Catalytic Antibody Specific for the CH2-CH3 Interdomain Region of Human IgE The peptide substrate ADSNPRGV (2.7 µM) is incubated with the catalytic antibodies produced by the procedure outlined above and the reaction monitored by reverse phase HPLC analysis of the mixture. Antibodies that show catalytic peptidase activity against the peptide substrate are treated for their ability to cleave IgE.

Assay for IgE Inactivation

Purified IgE anti-NP is subjected to digestion by the purified catalytic antibody, using 1 µg of IgE with 1 µg of catalytic antibody. The incubation is carried out in PBS(pH &0.5) for varying periods (hours to days) at 7° C. To control for nonspecificity in this reaction, noncatalytic monoclonal antibodies are included in parallel reactions.

To evaluate the cleavage, loss of basophil binding is studied. Samples (1–5 ng) of IgE anti-NP from the above digestion are incubated with a range of basophil cells ($6 \times 10^5 \cdot 10^7$ cells/ml) in 200 µl of RPMI 1640, 10% fetal calf serum and 10 mM EDTA for 15 at 37° C. These cells are then washed 3 times in the same buffer followed by addition of $^{35}$S-BSA-NIP (0.1 µCi) and further incubation for 15' at 37° C. The cells are washed and counted for radioactivity. Reduction or loss of $^{35}$S binding to the cells, relative to the IgE control incubations, demonstrates that cleavage of IgE has occurred.

Example V

Production of Abzyme Proteases Targeted to Tumor Necrosis Factor

Tumor necrosis factor (TNF) is a cytokine secreted by activated macrophages. TNF has been shown to mediate a variety of biological effects including endotoxin-induced shock, suppression of lipoprotein lipase (LPL) activity in preadipocytes, stimulation of collagenase activity and prostaglandin E2 production by synovial cells, stimulation of interleukin 1 production, and induction of cachexia in nude mice. TNF-specific cell-surface receptors are present on several types of cells. The binding of TNF to these receptors is believed necessary for induction of the biological effects of TNF. It has been shown that antibodies against amino acids 1–15 of hTNF block its binding to cell-surface receptors (Socher et al., Proc. Natl. Acad. Sci. USA, 1987 84, 8829–8833). It is also known that the N-terminal eight amino acids of hTNF are not required for receptor recognition. Consequently, the critical region for receptor binding may involve residues 9–15. The formula below shows the N-terminal 25 amino acids of TNF, the critical residues 9–15(*) and a metastable site NP, Asn-Pro.

VRSSSRTPSDKPVAHVVANPQAEGQ

Synthesis of the peptide analog containing the dipeptide isostere is performed essentially as previously described in Example IV. Synthesis of the metastable dipeptide isostere is essentially as described in Example II. Immunogen preparation, immunization, and screening for catalytic antibodies is performed essentially as described except that a bioassay is employed to determine TNF abzyme proteolysis and inactivation.

Tumor Necrosis Factor Cell Lysis Assay

Murine L-929 fibroblast cells (30,000 per well) are cultured in 96-well tissue culture plates in the presence of 1 µg/ml actinomycin D. Serial dilutions of TNF before and after treatment with the catalytic antibody are added to the wells and incubated for 18 hours. The culture medium is then removed and the cells stained with a 0.5% crystal violet solution in 25% methanol. The absorbance at 540 nm is measured on a Biotek ELISA microplate reader. The cells with medium alone are considered to have 0% lysis and the cells treated with 3M guanidine-HCL are considered to be completely lysed. One unit of TNF is defined as the amount required to give 50% cell lysis.

REFERENCES

1. T. Geiger and S. Clarke, *J. Biol. Chem.*, 1987, 262(2), 785–794.
2. S. Clarke, *Int. J. Pept. Protein Res.*, 1987, 30, 808–821.
3. A. A. Kossiakoff, *Science*, 1988, 240, 191–193.
4. A. Tramantano et al, *Science*, 1986, 234, 1566, R. Sugasawara, M. Powell, et al. *J. Am. Chem. Soc.*, 1987, 109, 2174.
5. D. Y. Jackson et al, *J. Am. Chem. Soc.*, 1988, 110 4841; D. Hilvert et al, *P.N.A.S. USA*, 1988, 85, 4953.
6. A. D. Napper, S. J. Benkovic, et al, *Science*, 1987, 237, 1041.
7. B. L. Iverson and R. A. Lerner, *Science*, 1989, 243, 1184–1187.
8. Socher, et al. *P.N.A.S. USA*, 1987, 84, 8829–8833.
9. Laskey, et al, *Cell*, 1987, 50, 975–985.
10. M. J. Darsley and A. R. Rees, *EMBO J.*, 1985, 4, 383–392.
11. R. C. Stephenson and S. Clarke, *J. Biol. Chem.*, 1989, 264, 6164–7170.
12. R. Lura and V. Schirch, *Biochemistry*, 1989, 27, 7671–77.
13. Laemmli, E. K. *Nature* 1970, 227, 630–635.
14. R. J. T. Corbett and R. S. Roche. *Int. J. Rept. Prot. Rel.*, 1986, 20, 549–559.
15. A. Fontana, *Biophysical Chem.*, 1988, 29, 181–193.
16. A. Fontana, et al. *Biochemistry.*, 1986, 25, 1847–1851.
17. J. K. Blodgett, et al., *J. Am. Chem. Soc.*, 1985, 107, 4305–4313.
18. C. van der Auwera and M. T. O. Anteuvius, *Int. J. Rept. Prot. Res.*, 1988, 31, 186–191.
19. ibid. *Int. J. Rept. Prot. Res.*, 1988, 31, 391–310.
20. D. Ho. *J. Virol.*, 61, 2024 (1987).
21. B. D. Walker et al., *P.N.A.S. USA*, 84, 8120.
22. Y. Vo. Quanq, *J. Med. Chem* 29, 579–587 (1986).
23. M. M. Campbell et al., *JCS Chem. Comm* p730 (1980).
24. R. N. Scribner, *Tetrahedron Letters* (1976) 3853–3856.
25. M. Kolb and B. Neises, *Tetrahedron Letters* 27, 4437–4440 (1986)
25b. J. F. Normant et al., *Bull. Soc. Chim. Fr*, (1974) 2072.
26. M. Bodanszky, *Principles of Peptide Synthesis*, Pub. Springer Verlag, Berlin (1984).

What is claimed is:

1. An antigen comprising an epitope for eliciting a catalytic antibody, wherein said catalytic antibody is immunologically cross reactive to an amino acid sequence of said epitope at or adjacent to the site of a naturally occurring metastable peptide bond, wherein said epitope comprises an analog of said metastable peptide bond, said analog comprising a chemical group selected from the group consisting of a difluoroketone, a phosphoramidate, and a phosphonate, wherein said chemical group mimics a substrate for metastable peptide bond hydrolysis.

2. An antigen as recited in claim 1, wherein said catalytic antibody enhances the rate of reaction of a substrate of interest having a metastable peptide bond and said analog antigenically mimics said metastable peptide bond at or adjacent to the site of the metastable peptide bond in said substrate of interest.

3. An antigen as recited in claim 1 wherein the metastable peptide bond is selected from the group consisting of ASN-X, ASP-X, GLN-X, GLU-X, LYS-X, and HIS-Y-X, wherein X and Y are any amino acid.

4. An antigen as recited in claim 1 wherein said antigen comprises an amino acid sequence of at least two amino acids.

5. An antibody elicited by an antigen as recited in claim 1.

6. An antibody which enhances the rate of modification of a naturally occurring metastable peptide bond in a substrate of interest, said antibody having been prepared by a process comprising the steps of:
 (a) selecting a naturally occurring metastable peptide bond to be modified in a substrate of interest;
 (b) selecting an antigen comprising an epitope for eliciting an antibody capable of enhancing the modification of said metastable peptide bond, wherein said epitope comprises an analog of said metastable peptide bond, which analog comprises a chemical group selected from the group consisting of a difluoroketone, a phosphoramidate, and a phosphonate, and said chemical group mimics a substrate for metastable peptide bond hydrolysis;
 (c) exposing cells capable of producing antibodies to said antigen and thereby generating antibody producing cells;
 (d) hybridizing said antibody producing cells with myeloma cells and thereby generating a plurality of hybridoma cells each producing monoclonal antibodies; and
 (e) screening said plurality of monoclonal antibodies to identify a monoclonal antibody which enhances the rate of modification of said metastable peptide bond, wherein said antibody is immunologically cross reactive to an amino acid sequence at or adjacent to the site of said metastable peptide bond.

7. An antibody as recited in claim 6 wherein the metastable bond is selected from the group consisting of ASN-X, ASP-X, GLN-X, GLU-X, LYS-X, and HIS-Y-X, wherein X and Y are any amino acid.

8. A method for preparing antibodies which enhance the rate of cleavage or formation of a naturally occurring metastable peptide bond of interest comprising the steps of:
 (a) selecting a naturally occurring metastable peptide bond to be cleaved or formed in a protein or peptide substrate of interest;
 (b) selecting an antigen comprising an epitope for eliciting an antibody capable of enhancing the modification of said metastable peptide bond, wherein said epitope comprises an analog of said metastable peptide bond, which analog comprises a chemical group selected from the group consisting of a difluoroketone, a phosphoramidate, and a phosphonate, and said chemical group mimics a substrate for metastable peptide bond hydrolysis;
 (c) exposing cells capable of producing antibodies to said antigen and thereby generating antibody producing cells;
 (d) hybridizing said antibody producing cells with myeloma cells and thereby generating a plurality of hybridoma cells each producing monoclonal antibodies; and
 (e) screening said plurality of monoclonal antibodies to identify a monoclonal antibody which enhances the rate of modification of said metastable peptide bond, wherein said antibody is immunologically cross reactive to an amino acid sequence at or adjacent to the site of said metastable peptide bond.

9. A method for enhancing the rate of modification of a naturally occurring metastable peptide bond within a protein or peptide substrate of interest which comprises
 contacting said substrate with an antibody which enhances the rate of reaction of the substrate at the metastable peptide bond, said contacting being under conditions sufficient for said antibody to bind to said substrate at an epitope positioned at or adjacent to said metastable peptide bond and to enhance the rate of reaction thereat, wherein said antibody is immunologically cross reactive to an amino acid sequence of said epitope at or adjacent to the site of said metastable peptide bond and said epitope comprises an analog of said metastable peptide bond, said analog comprising a chemical group selected from the group consisting of a difluoroketone, a phosphoramidate, and a phosphonate and said chemical group mimics a substrate for metastable peptide bond hydrolysis.

10. A method for enhancing the rate of modification of a naturally occurring metastable peptide bond within a protein or peptide substrate of interest which comprises
 contacting said substrate with an effective amount of an antibody which enhances the rate of reaction of the substrate at the metastable peptide bond, said contacting being under conditions sufficient for said antibody to bind to said substrate at an epitope at or adjacent to said metastable peptide bond, and thereby enhance the rate of said reaction thereat, said antibody having been produced by the method of:
 (a) selecting a naturally occurring metastable peptide bond to be cleaved or formed in a protein or peptide substrate of interest;
 (b) selecting an antigen comprising an epitope for eliciting an antibody capable of enhancing the modification of the metastable peptide bond, wherein said epitope comprises a an analog of said metastable peptide bond, said analog comprises a chemical group selected from the group consisting of a difluoroketone, a phosphoramidate, and a phosphonate, said chemical group being positioned at or adjacent to the site of said metastable peptide bond and the chemical group mimics a substrate for metastable peptide bond hydrolysis;
 (c) exposing cells capable of producing antibodies to said antigen and thereby generating antibody producing cells;
 (d) hybridizing said antibody producing cells with myeloma cells and thereby generating a plurality of hybridoma cells each producing monoclonal antibodies; and
 (e) screening said plurality of monoclonal antibodies to identify a monoclonal antibody which enhances the rate of modification of said metastable bond, wherein said antibody is immunologically cross reactive to an amino acid sequence at or adjacent to the site of said metastable peptide bond.

11. A method as recited in claim 10 wherein the protein or peptide substrate of interest to be modified includes an amino acid sequence selected from the group consisting of ASN-X, ASP-X, GLN-X, GLU-X, LYS-X, and HIS-Y-X, wherein X and Y are any amino acid.

12. The antigen of claim 1 further comprising a carrier.

* * * * *

UNITED STATES PATENT AND TRADEMARK OFFICE
CERTIFICATE OF CORRECTION

PATENT NO.    : 6,521,432 B1
DATED         : February 18, 2003
INVENTOR(S)   : Powell et al.

It is certified that error appears in the above-identified patent and that said Letters Patent is hereby corrected as shown below:

<u>Title page,</u>
Item [56], U.S. PATENT DOCUMENTS, change "5,190,805 A" to -- 5,190,865 A --

<u>Column 3,</u>
Line 64, delete "," after "comprised"

<u>Column 4,</u>
Line 2, change "AND" to -- and --

<u>Column 7,</u>
Line 33, insert -- in -- between "propagated" and "in"

<u>Column 11,</u>
Line 38, delete "." after "Similar"

<u>Column 19,</u>
Line 15, change "&0.5)" to -- 7.5) --
Line 16, change "7° C." to -- 37° C. --

<u>Column 20,</u>
Line 18, change "," after "1566" to -- ; --
Line 21, insert -- , -- after "110"

<u>Column 21,</u>
Line 31, change "." after "difluoroketone" to -- , --

<u>Column 22,</u>
Line 49, delete "a" between "comprises" and "an"

UNITED STATES PATENT AND TRADEMARK OFFICE
CERTIFICATE OF CORRECTION

PATENT NO.    : 6,521,432 B1
DATED         : February 18, 2003
INVENTOR(S)   : Powell et al.

It is certified that error appears in the above-identified patent and that said Letters Patent is hereby corrected as shown below:

<u>Column 23,</u>
Line 4, delete "to be modified"

Signed and Sealed this

Ninth Day of September, 2003

JAMES E. ROGAN
*Director of the United States Patent and Trademark Office*